United States Patent [19]

Bertola et al.

[11] Patent Number: 5,069,687

[45] Date of Patent: Dec. 3, 1991

[54] PROCESS OF RECOVERY OF MALEIC ANHYDRIDE FROM REACTION GASEOUS MIXTURES

[75] Inventors: Aldo Bertola, Milan; Roberto Ruggieri, Basiglio, both of Italy

[73] Assignee: Sisas Societa Italiana Serie Acetica E Sintetica SPA, Milan, Italy

[21] Appl. No.: 587,080

[22] Filed: Sep. 24, 1990

[30] Foreign Application Priority Data

May 31, 1990 [IT] Italy .............................. 20504 A/90

[51] Int. Cl.[5] .............................................. B01D 47/00

[52] U.S. Cl. .......................................... 55/44; 55/48; 55/75; 55/53; 549/262

[58] Field of Search ................... 55/80, 84, 85, 48, 53, 55/44, 75; 549/262, 256, 257; 203/49, 14, 15

[56] References Cited

U.S. PATENT DOCUMENTS 4,118,403 10/1978 White ................................. 549/262
4,199,410 4/1980 Ohrui et al. .......................... 203/49

*Primary Examiner*—Bernard Nozick
*Attorney, Agent, or Firm*—Nixon & Vanderhye

[57] ABSTRACT

Process for the recovery of maleic anhydride from a gaseous mixture thereof, in which the gaseous mixture containing maleic anhydride is contacted with an absorbant for the maleic anhydride to give an enriched absorbant. Water present in the enriched absorbant is then substantially removed by contacting the enriched absorbant with a water adsorbant or with a low humidity stripping gas to produce a dried enriched absorbant. The maleic anhydride is then recovered from the dried enriched absorbant.

9 Claims, No Drawings

PROCESS OF RECOVERY OF MALEIC ANHYDRIDE FROM REACTION GASEOUS MIXTURES

The present invention relates to the recovery of maleic anhydride from reaction mixtures resulting from the catalytic oxidation of butane, butene, mixtures of hydrocarbons containing four carbon atoms or benzene, by means of air at high temperatures.

The maleic anhydride so produced is in diluted gaseous form at the outlet of the oxidation reactor and must be recovered.

BACKGROUND OF THE INVENTION

A first method to carry out this recovery consists in the absorption of the maleic anhydride with water: it reacts with the water to form maleic acid which is thus in form of a solution capable of attaining a concentration up to about 50%. After separation of the water by distillation maleic anhydride is recovered by dehydration of the maleic acid.

The effectiveness of this process has been improved by adding a partial condenser upstream of the water washing, since by lowering the temperature of the gaseous mixture below the dew point of the maleic anhydride, part thereof condenses and the recovery is only devoted to the residual portion remaining in the gaseous phase.

However this type of recovery is affected by a number of drawbacks, among which the following are worthy of note:

the distillation of the water and the dehydration of the maleic acid cause a great energy consumption;

part of the product is lost owing to the conversion of maleic acid into fumaric acid;

in turn the fumaric acid is solid whereby the absorption apparatus is fouled thereby, thus causing the plant to be often stopped for the washing operations.

Alternatively it has been proposed a long time ago to effect this recovery through absorption in an organic solvent.

Such an organic solvent, preferably dibutyl phthalate, was firstly used for the absorption of mixtures of phthalic anhydride and maleic anhydride resulting from the oxidation of hydrocarbons, such as for example o-xylene, benzene and naphthalene (see for instance U.S. Pat. No. 2,942,005 and other patents).

Thereafter the attention was focused on the recovery of maleic anhydride only, obtained through the catalytic oxidation of butane, butene or mixtures of $C_4$ hydrocarbons. U.S. Pat. No. 3,981,680 to Chevron Research Co. discloses a process according to which the reaction gaseous mixture is contacted with a liquid phase at least mainly consisting of a dialkyl phthalate having 4 to 8 carbon atoms in each alkyl group and a total of 10 to 14 carbon atoms in the two alkyl groups taken together.

In turn U.S. Pat. No. 4,118,403 to Monsanto Co. discloses a like process, except that the liquid absorbing phase is added with a critical amount of phthalic anhydride permitting the temperature to which the solvent may be heated to be controlled and leading at the very end to a recovery of maleic anhydride from the gaseous reaction mixture higher than 98%.

Among the advantages originating from the organic solvent process the following are worth mentioning.

lower amount of byproducts and mainly of fumaric acid, which causes a higher purification yield in comparison with the standard process of absorption with water;

lower energy consumption, since the evaporation of relevant amounts of water is avoided;

lower amounts of aqueous effluents, mainly originated from the water washing for the solid removal, such as the fumaric acid, a depuration treatment being necessary for these effluents.

Thus, as a matter of fact, in the solvent process as practiced to date the mixture of reaction gases is passed through an absorption column in which it comes into contact with the organic solvent in liquid form by which the maleic anhydride is absorbed.

The thus enriched solvent is passed to a separating apparatus for the maleic anhydride, the latter being transferred to the purification step, whereas the impoverished solvent is recycled to the absorption column. However, before such a recycling, the solvent in which heavy products build up is washed with water.

Even by adopting the above mentioned measures some problems and drawbacks still exist among which, firstly, that of the even modest absorption of water by the solvent before it is passed to the separation of the maleic anhydride and recycled to the absorber. This water, as a matter of fact causes the solvent to be decomposed and a certain amount of fumaric acid to be formed at expenses of the maleic anhydride to be recovered, whereby not only the recovery yield is reduced, but the problems of the fouling of the absorber, of the maleic anhydride separator and of the heat exchanger due to the solid fumaric acid being deposited still are present although in a lower degree.

DESCRIPTION OF THE INVENTION

It has been found and is the object of the present invention that the above problems and drawbacks are essentially done away with by carrying out a dehydration of the solvent enriched with maleic anhydride and coming out of the absorber, before effecting the separation of the maleic anhydride and thus before this solvent enriched with maleic anhydride is brought to conditions, particularly of temperature, promoting the solvent decomposition and the forming of fumaric acid.

Thus the present invention, according to the preferred embodiment provides a process for the recovery of maleic anhydride, of the type in which the gaseous reaction mixture is contacted with an organic solvent adapted for the absorption of the maleic anhydride contained in said gaseous mixture and said solvent enriched with maleic anhydride is passed to a separation step of the maleic anhydride from said enriched solvent, the impoverished solvent being recycled to the absorption step, characterized in that, before the separation phase, the water contained in said enriched solvent is removed by contacting it with a low relative humidity gas, the operation being carried out at a pressure of between 0.01 and 2.0 bar and at a temperature higher than 80° C. and anyhow suitable to permit the evaporation of the water contained in said enriched solvent.

The gases which can be used are nitrogen and/or air and/or carbon dioxide with a water percentage up to 15%.

Alternatively the water removal can take place by passing on adsorbents of several types. The preferred adsorbing agent is a standard zeolite used for the dehydration of organic solvents. The use of zeolite permits not only a complete dehydration to be obtained, but also the light acids present in the solvent to be removed.

The acids can be recovered through the stripping of the zeolite with a gas in a closed cycle, it being of interest owing to their commercial value.

By the process of the present invention the further advantage is achieved of the removal, together with the water, of most of the lightest compounds, such as for example the acrylic acid and others which might polymerize or copolymerize forming fouling solid products which in this manner are prevented from reaching the purification step, thus contributing to improve the product quality.

Experimental tests have been effected with the process of the present invention by varying the flow rate of the stripping gas and/or the temperature thereof. In the following table the concentrations of water and of acrylic acid (taken as the index of the light compounds) as measured in the enriched solvent both at the inlet and at the outlet of the stripping phase:

| ENRICHED SOLVENT | | | | | |
|---|---|---|---|---|---|
| BEFORE STRIPPING | | AFTER THE STRIPPING | | GAS FLOWRATE | |
| WATER | ACRYLIC ACID | WATER | ACRYLIC ACID | GAS MOLES SOLVENT MOLES | TEMPERATURE |
| 0.21% | 0.04 | 0.08% | 0.01 | 1.2 | 120 |
| 0.30% | 0.05 | 0.07% | 0.01 | 1.8 | 120 |
| 0.20% | 0.03 | 0.10% | 0.01 | 1.2 | 100 |
| 0.18% | 0.04 | 0.08% | 0.01 | 1.8 | 100 |
| 0.25% | 0.03 | 0.06% | inf. 0.01 | 1.2 | 150 |
| 0.20% | 0.05 | 0.04% | inf. 0.01 | 1.8 | 150 |

From the data the results achieved by the present invention are evident, especially if account is taken of the fact that the reduction of the water concentration involves a corresponding reduction of the amounts of decomposed solvent and of the maleic anhydride being lost in the form of fumaric acid.

More particularly, in the case in which the solvent is dibutyl phthalic, the far less decomposition of the solvent permits the amount of phthalic anhydride in the solvent to be maintained at concentrations less than 0.5%, typical values being of between 0.1% and 0.4%.

Industrial experiments, based on the use of dibutyl phthalic as the solvent, gave the following typical values of phthalic anhydride contained in the solvent and of quality of the raw maleic anhydride obtained after the separation in a vacuum column:

| PHTHALIC ANHYDRIDE CONTENT IN THE ENRICHED SOLVENT | PRESENCE OF SOLVENT IN RAW MALEIC ANHYDRIDE |
|---|---|
| 0.2% | <0.1% |
| 0.3% | <0.1% |
| 0.4% | <0.1% |

In this manner it has been demonstrated that a good separation between dibutyl phtalate as the solvent and maleic anhydride can be obtained even if the operation is not carried out in the presence of relevant concentrations of phthalic anhydride.

As a confirmation in an industrial test with dibutyl phthalic as the solvent, the dehydration of the enriched solvent (flow rate 25 ton/h; water content 0.4%) has been effected by using 3000 Ncm/H of air at a temperature of the air of 120° C.

At the outlet of the column, the solvent, dibutyl phthalic, had a water content less than 0.1%.

Besides the evident advantage of reducing the losses of solvent (by decomposition) and of maleic anhydride (owing to the conversion to fumaric acid) other advantages are achieved by the invention.

As a matter of fact an easier washing of the solvent (which is necessary for the removal of the water soluble acids) is permitted due to the lower amount of acids to be removed. Moreover as an additional advantage, if the solvent is an ester, the decomposition thereof would lead to the forming of the corresponding alcohol which would remain in the raw maleic anhydride and would tend to form maleates, by which the product quality is worsened, or the purification thereof is made more difficult.

The above description is evidently referred to a preferred and industrially advantageous embodiment, but alternative methods adapted to achieve the same result are possible and foreseable, namely in order to dehydrate as much as possible the solvent enriched with maleic anhydride and coming from the absorbing step, before it is passed to the phase of separation of the absorbed maleic anhydride.

We claim:

1. A process for the recovery of maleic anhydride from a gaseous mixture thereof, said process comprising the steps of:

(a) contacting the aqueous mixture containing maleic anhydride with an liquid absorbant for the maleic anhydride to give an enriched liquid absorbant;

(b) contacting the enriched liquid absorbant from (a) with a water adsorbant to reduce the water content of said enriched liquid absorbant to produce a dried enriched liquid absorbant; and then (c) recovering the maleic anhydride from the dried enriched liquid absorbant from (b).

2. A process according to claim 1, wherein said liquid absorbant for the maleic anhydride is dibutylphthalate.

3. A process according to claim 2, wherein said adsorbant is a zeolite material.

4. A process for the recovery of maleic anhydride from a gaseous mixture thereof, said process comprising the steps of:

(a) contacting the gaseous mixture containing maleic anhydride with an liquid absorbant for the maleic anhydride to give an enriched liquid absorbant;

(b) contacting the enriched liquid absorbant from (a) with a low humidity stripping gas to reduce the water content of said enriched absorbant to produce a dried enriched liquid absorbant; and then (c) recovering the maleic anhydride from the dried enriched liquid absorbant from (b).

5. A process according to claim 4, wherein said liquid absorbant is dibutylphthalate.

6. A process according to claim 4, wherein said enriched liquid absorbant is contacted with said low humidity stripping gas at a pressure of 0.01 to 2.0 bar.

7. A process according to claim 6, wherein said process is carried out at a temperature higher than 80° C.

8. A process according to claim 7, wherein said temperature is 100° C. to 150° C.

9. A process according to claim 4, wherein said low humidity stripping gas is selected from the group consisting of nitrogen, air and carbon dioxide.

* * * * *

UNITED STATES PATENT AND TRADEMARK OFFICE

CERTIFICATE OF CORRECTION

PATENT NO. : 5,069,687

DATED : December 3, 1991

INVENTOR(S) : BERTOLA et al

It is certified that error appears in the above-identified patent and that said Letters Patent is hereby corrected as shown below:

Column 3 line 65 delete "phthalic" and replace by --phthalate--

Column 4 line 2 delete "phthalic" and replace by --phthalate--

Column 4 line 42 delete "aqueous" and replace by --gaseous--

Signed and Sealed this

Eighth Day of June, 1993

Attest:

MICHAEL K. KIRK

*Attesting Officer*

*Acting Commissioner of Patents and Trademarks*